US00PP13809P39

(12) United States Plant Patent
MacCormick

(10) Patent No.: US PP13,809 P3
(45) Date of Patent: May 13, 2003

(54) VARIETY OF CANNA NAMED 'MACTRO'

(76) Inventor: Neil MacCormick, 7 Richardson Road, Alfriston, R.D., Manurewa, Auckland (NZ)

( * ) Notice: Subject to any disclaimer, the term of this patent is extended or adjusted under 35 U.S.C. 154(b) by 0 days.

(21) Appl. No.: 09/956,441

(22) Filed: Sep. 18, 2001

(65) Prior Publication Data

US 2003/0056258 P1 Mar. 20, 2003

(51) Int. Cl.[7] ..... A01H 5/00
(52) U.S. Cl. ..... Plt./263
(58) Field of Search ..... Plt./263

(56) References Cited

U.S. PATENT DOCUMENTS

PP10,569 P * 8/1998 Potgieter ..... Plt./263

* cited by examiner

*Primary Examiner*—Bruce R. Campell
*Assistant Examiner*—W C Haas
(74) *Attorney, Agent, or Firm*—Fulwider Patton Lee & Utecht, LLP

(57) ABSTRACT

A new and distinct cultivar of canna plant named 'MACtro' characterized by a dark to yellow-green leaf pattern having multiple linear inter-veinal stripes ranging from a yellow-green coloring which fades to a green-white as the plant matures and a prominent creamy yellow midrib. The leaves offering a vivid contrast to the yellow-orange flowers.

1 Drawing Sheet

BACKGROUND OF THE NEW PLANT

The present invention comprises a new and distinct cultivar of canna, botanically known as *Canna hybrida* and further known by the varietal name 'MACtro' (Anthony Tesselaar International No. 011/C). The new variety was discovered in a selective breeding program by Neil MacCormick in Manurewa, Auckland, New Zealand. The new variety is a selection from the open pollenation of Canna 'Phasion' (U.S. Plant Pat. No. 10,569) providing both the male and female pollen parents. The new cultivar was selected from the progeny by the inventor Neil MacCormick in Auckland, New Zealand.

The new variety is the result of a selective breeding program taken from selected seedlings in a property in Manurewa, Auckland, New Zealand in the year 2000. These seedlings were selected and propagated through rhizome divisions selecting for differences in color variation of the interveinal striping.

The new cultivar has since been asexually reproduced by rhizome divisions in Manurewa, Auckland, New Zealand and has been repeatedly asexually reproduced by divisions in Manurewa, Auckland, New Zealand. Continued observations from the vegetative divisions have confirmed that the distinguishing features of this new cultivar came true, remain stable and are retained through successive propagation.

The new cultivar was grown in a closed, heated greenhouse in Manurewa, Auckland, New Zealand. It is typically grown under natural light conditions in pots in a bark based potting media. Typical time from division to flowering is 6 months.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth characteristics of the new cultivar. The data which defines each characteristic was collected from asexual reproductions grown outdoors, carried out in Manurewa, Auckland, New Zealand. The plant histories were taken on rooted divisions believed to have been potted in a 25 cm pot on approximately November 2000 and flowering in the first growing season on approximately February, 2001 outdoors and color readings were taken in daylight using The Royal Horticultural Society of London Colour Chart, 1995.

THE PLANT

Classification:

*Botanical.*—*Canna hybrida.*

*Commercial.*—'MACtro'.

*Parentage.*—Seed Parent — Canna hybrid 'Phasion'. Pollen Parent — both male and female are Canna 'Phasion'. Origin — Selected seedling. Propagation — Rhizome division, rhizomes are creeping and fibrous. Rooting habit — Issuing from rhizomes.

Form:

*Type.*—Dense, clump forming, slow growing rhizomatous herb.

*Height.*—Up to 2000 mm.

*Width.*—Up to 800 mm.

*Growth rate and habit.*—Upright growth habit; medium in size; growth rate is fast. Grows to full height in single growing season.

*Strength.*—Free standing.

*Stem.*—Size: — 25 mm in diameter. Color: — Yellow Green Group RHS 153C.

Leaves:

*Arranged.*—Spirally.

*Shape.*—Lamina is large, ovate and broad elliptic, entire and multi-colored, aspect of the leaf is 45 degrees to nearly vertical, venation and midrib are prominent.

*Length.*—Average 400 mm.

*Width.*—Average 220 mm at its widest point.

*Margin.*—Entire.

*Texture.*—Smooth.

*Color.*—Generally — Dark grey-green to light yellow-green green with alternating interveinal yellow-green stripes which fade to creamy yellow as the plant matures. Interveinal stripes begin at the midrib of the blade and extend upwardly and outwardly towards the outer edges or tips of the leaves, with the shape and color of the stripes being irregular; green zone of upper side of leaf varies from Green Group RHS 137C to Green Group RHS 137A at maturity; green zone of lower side of leaf from Green Group 137B.

Interveinal:

*Zones.*—Generally — Yellow-green stripes on the upper and lower sides starting from Yellow-Green Group RHS 153D and fading to creamy yellow at maturity then Green-White Group RHS 157C.

*Midrib.*—Prominent, Yellow-Green Group RHS 153C.

INFLORESCENCE

General: Inflorescence is a terminal raceme about 300 to 450 mm long, almost branching to second main axis which may be as large as the main axis; main axis always flowers before secondary axis; bracteate, with upper bracts subtending solitary or parred sessile or very short pedicellate. Flowers are bi-sexual, asymmetric, and showy, and are about 130 mm across. Flowering time is May to September — depending on local climatic and environmental conditions. Duration of flowering is typically 2–3 months.

Borne: Terminal raceme about 300–450 mm long.

Bud:

*Shape.*—Lanceolate.

Sepal:

*Quantity.*—Three in number.

*Length.*—35 mm.

*Width.*—10 mm.

*Form.*—Oval to elliptic, top is rounded off.

Petals: Time of flowering early to late with long flowering time.

*Quantity.*—3 unequal united in a basal tube.

*Size.*—Large.

*Arrangement.*—Overlapping.

*Length.*—85 mm.

*Width.*—Up to 20 mm wide at widest point.

*Color.*—Midzone outside — Yellow-Orange Group RHS17B. Midzone inside — Yellow-Orange Group RHS17B. Margin inside — Yellow Group RHS4B.

Flowers:

*Quantity.*—Approximately 17 flower buds per stem.

*Size.*—Approximately 100 mm.

*Profile upper.*—Irregular.

*Profile lower.*—Irregular.

*Color.*—Generally yellow-orange from Yellow-Orange Group RHS17B; variegation and margin are closest to Yellow Group RHS4B.

Bract:

*Color.*—Violet-Blue Group RHS92A.

Fragrance: None detected.

Persistence:

*Disease resistance.*—No known specific disease resistence.

REPRODUCTIVE ORGANS

Stamens: Single stamen is petaloid with solitary marginal anther, united to fleshy-style; staminoides are two in number with one almost as big as petal and same color, recurved; nectarial glands present; ovary inferior, three locular, verrucose, ovules numerous, style petaloid.

Filaments:

*Color.*—Ranging from Orange Group RHS24A to Orange Group RHS25A.

Anther: Solitary marginal anther Orange Group RHS28A.

Pistils:

*Style.*—Orange Group RHS28A.

Fruit:

*Size.*—Up to 20 mm, not fully developed, verrucose, capsule.

*Color.*—Immature — Green Group RHS137A. Mature — Red-Purple Group RHS178A.

*Seeds.*—Do not develop.

GENERAL CHARACTERISTICS

'MACtro' is primarily distinguished from its parent Canna 'Phasion' and other hybrid cultivars of Canna genus by the alternatively striped or interveinal coloring of its leaves. More specifically 'MACtro' takes the form of a slow growing perennial herb with horizontal subterranean rhizomes with multiple striped or interveinal leaves, and its creamy yellow midrib. The leaf is dark green with interveinal stripes ranging from yellow-green stripes which fade to a creamy yellow as the plant matures. The interveinal stripes of 'MACtro' begin at the midrib of each leaf and extend upwardly and outwardly toward the edges or tips of the leaves, with the shape and color of the stripes being irregular. The green leaves and interveinal striping providing a rich background contrast to the yellow-orange flowers. Typically 'MACtro' has approximately 8–10 racemes per year of growth.

I claim:

1. A new and distinct variety of Canna plant, substantially as shown and described.

* * * * *

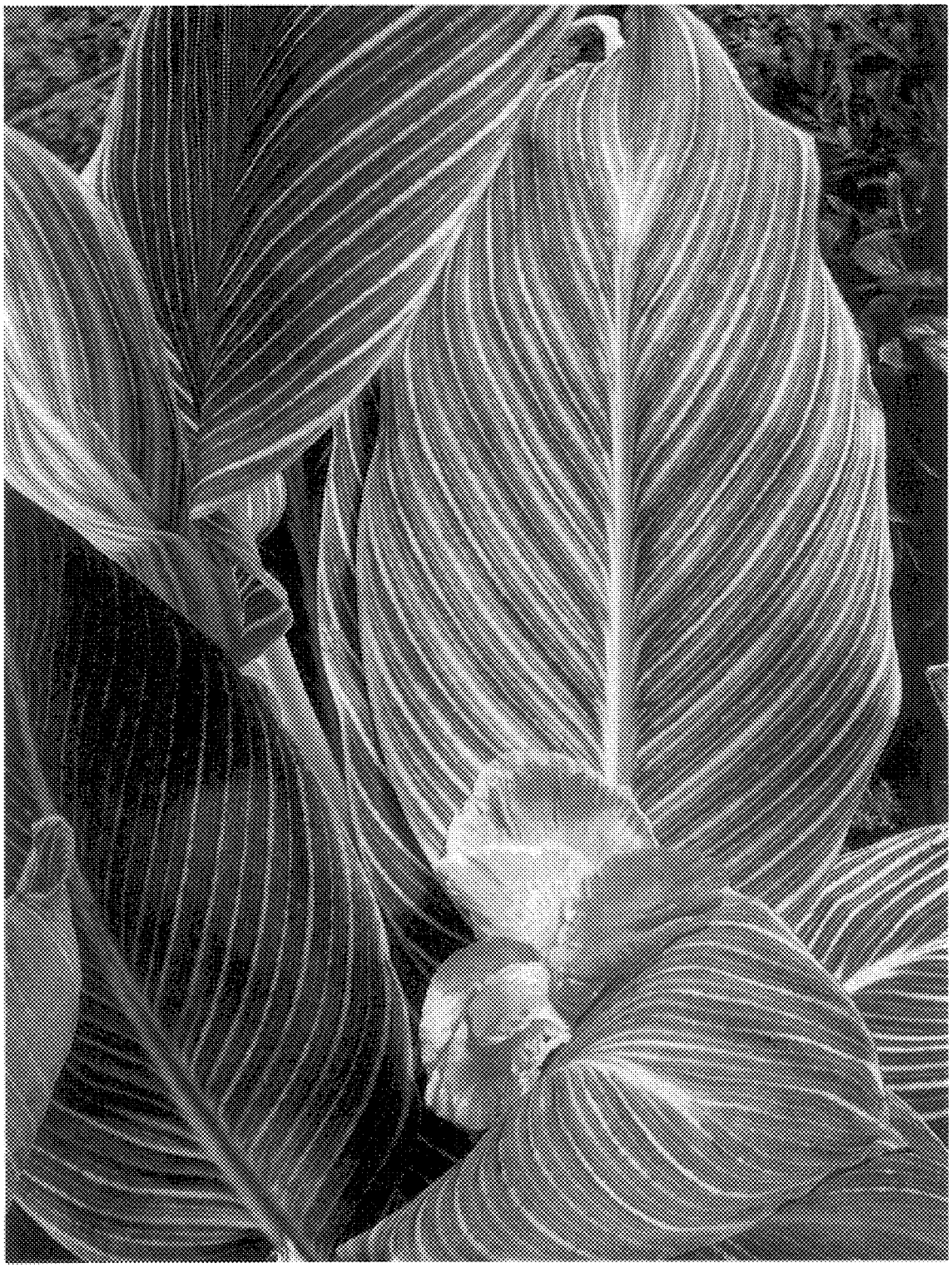

UNITED STATES PATENT AND TRADEMARK OFFICE

CERTIFICATE OF CORRECTION

PATENT NO. : PP 13,809 P3
DATED : May 13, 2003
INVENTOR(S) : Neil MacCormick

It is certified that error appears in the above-identified patent and that said Letters Patent is hereby corrected as shown below:

Column 1,
Line 6, delete, "in a selective breeding program"
Line 8, replace, "variety is" with -- variety, which arose by spontaneous sport or mutation,is --
Lines 13-18, delete, "The new variety is the result of a selective breeding program taken from selected seedlings in a property in Manurewa, Auckland, New Zealand in the year 2000. These seedlings are selected and propagated through rhizome divisions selecting for differences in color variation of the interveinal striping."

Signed and Sealed this

Twenty-sixth Day of July, 2005

JON W. DUDAS
*Director of the United States Patent and Trademark Office*